(12) United States Patent
Tarasek et al.

(10) Patent No.: US 10,405,773 B2
(45) Date of Patent: Sep. 10, 2019

(54) TISSUE DELINEATION AND CHARACTERIZATION IN MAGNETIC RESONANCE IMAGING

(71) Applicants: GENERAL ELECTRIC COMPANY, Schenectady, NY (US); MEMORIAL SLOAN-KETTERING CANCER CENTER, New York, NY (US)

(72) Inventors: Matthew Richard Tarasek, Niskayuna, NY (US); Thomas Kwok-Fah Foo, Clifton Park, NY (US); Desmond Teck Beng Yeo, Niskayuna, NY (US); Oguz Akin, New York, NY (US)

(73) Assignee: General Electric Company, Schenectady, NY (US)

( * ) Notice: Subject to any disclaimer, the term of this patent is extended or adjusted under 35 U.S.C. 154(b) by 1300 days.

(21) Appl. No.: 14/577,770

(22) Filed: Dec. 19, 2014

(65) Prior Publication Data
US 2016/0174868 A1   Jun. 23, 2016

(51) Int. Cl.
*G01R 33/48* (2006.01)
*A61B 5/055* (2006.01)
(Continued)

(52) U.S. Cl.
CPC .......... *A61B 5/055* (2013.01); *A61B 5/0051* (2013.01); *A61B 5/0053* (2013.01); *A61B 5/01* (2013.01); *A61B 5/4836* (2013.01); *A61B 5/7278* (2013.01); *A61B 5/7282* (2013.01); *A61F 7/02* (2013.01); *A61N 7/02* (2013.01); *G01R 33/4804* (2013.01); *A61F 2007/0054* (2013.01);
(Continued)

(58) Field of Classification Search
CPC ............ G01R 33/4816; G01R 33/4818; G01R 33/482; G01R 33/4822; G01R 33/4824; G01R 33/4826; G01R 33/4828; G01R 33/483; G01R 33/4831; G01R 33/4833; G01R 33/4835; G01R 33/4836; G01R 33/4838; G01R 33/50; G01R 33/543; G01R 33/5602; G01R 33/5604; G01R 33/5605; G01R 33/5607; G01R 33/5608; G01R 33/561; G01R 33/5611; G01R 33/5612; G01R 33/5613; G01R 33/5614; G01R 33/5615; G01R 33/5616; G01R 33/5617
See application file for complete search history.

(56) References Cited

U.S. PATENT DOCUMENTS 5,284,144 A    2/1994  Delannoy et al.
8,376,946 B2   2/2013  Littrup et al.
(Continued)

OTHER PUBLICATIONS

Moller, U., et al.; "Temperature and Blood Flow Measurements in and around 7,12-Dimethyibenz(a)anthracene-induced Tumors and Walker 256 Carcinosarcomas in Rats", Cancer Research, vol. 35, pp. 3116-3121, Nov. 1975.
(Continued)

*Primary Examiner* — Tung X Nguyen

(57) ABSTRACT

The present disclosure describes non-invasive approaches for delineating and characterizing tissue using MR imaging over a range of treatment levels. By way of example, tumor tissue may be distinguished and delineated from other tissue, such as muscle tissue. Further, tumor tissue may be characterized as malignant or benign using such approaches.

10 Claims, 4 Drawing Sheets

(51) Int. Cl.
  *A61B 5/00* (2006.01)
  *A61N 7/02* (2006.01)
  *A61B 5/01* (2006.01)
  *A61F 7/02* (2006.01)
  *G01R 33/50* (2006.01)
  *G01R 33/56* (2006.01)
  *G01R 33/563* (2006.01)
  *A61F 7/00* (2006.01)

(52) U.S. Cl.
  CPC ............ *A61F 2007/0071* (2013.01); *A61F 2007/0095* (2013.01); *A61F 2007/0295* (2013.01); *G01R 33/50* (2013.01); *G01R 33/5608* (2013.01); *G01R 33/56341* (2013.01)

(56) References Cited

U.S. PATENT DOCUMENTS

| | | | |
|---|---|---|---|
| 2007/0110293 A1 | 5/2007 | Arnon | |
| 2010/0056944 A1 | 3/2010 | Keith et al. | |
| 2010/0075925 A1 | 3/2010 | Torti et al. | |
| 2011/0108702 A1 | 5/2011 | Jackson et al. | |
| 2011/0268332 A1 | 11/2011 | Hofstetter et al. | |
| 2013/0281826 A1 | 10/2013 | Carasso et al. | |
| 2015/0016682 A1* | 1/2015 | Levy | A61N 7/02 382/103 |
| 2018/0020926 A1* | 1/2018 | Stang | A61B 5/015 600/439 |

OTHER PUBLICATIONS

Parker, Dennis, L.; "Applications of Nmr Imaging in Hyperthermia: An Evaluation of the Potential for Localized Tissue Heating and Noninvasive Temperature Monitoring", Biomedical Engineering, IEEE Transactions on, vol. BME-31, Issue 1, pp. 161-167, Jan. 1984.

Caravan, Peter, et al.; "Gadolinium(III) Chelates as MRI Contrast Agents: Structure, Dynamics, and Applications", Chemical Reviews, vol. 99, Issue 9, pp. 2293-2352, Sep. 1999.

Golman, K., et al.; "Molecular imaging using hyperpolarized 13C", The British Journal of Radiology, 76 Spec No. 2: S118-27, 2003.

Choyke, Peter L., et al.; "Functional Tumor Imaging With Dynamic Contrast-Enhanced Magnetic Resonance Imaging", Journal of Magnetic Resonance Imaging, vol. 17, pp. 509-520, 2003.

Simonetti, Arjan W., et al.; "Combination of Feature-Reduced MR Spectroscopic and MR Imaging Data for Improved Brain Tumor Classification", NMR in Biomedicine NMR Biomed, vol. 18, pp. 34-43, 2005.

Rieke, Viola, et al.; "MR Thermometry", Journal of Magnetic Resonance Imaging, vol. 27, Issue 2, pp. 376-390, Feb. 2008.

Zhao, Qi, et al.; "Use of a Thermocouple for Malignant Tumor Detection", Engineering in Medicine and Biology Magazine, IEEE, vol. 27, issue 1, pp. 64-66, Feb. 2008.

Wu, Jim S., et aL; "Soft-tissue tumors and tumorlike lesions: a systematic imaging approach", Radiology, vol. 253, Issue 2, pp. 297-316, Nov. 2009.

Jenista, Elizabeth R., et al.; "Absolute temperature imaging using intermolecular multiple quantum MRI", International journal of hyperthermia : the official journal of European Society for Hyperthermic Oncology, North American Hyperthermia Group, vol. 26, Issue 7, pp. 725-734, 2010.

Chenevert, Thomas L., et al.; "Diffusion coefficient measurement using a temperature-controlled fluid for quality control in multi-center studies", Journal of Magnetic Resonance Imaging, vol. 34, Issue 4, pp. 983-987, Oct. 2011.

\* cited by examiner

TISSUE DELINEATION AND CHARACTERIZATION IN MAGNETIC RESONANCE IMAGING

BACKGROUND

In general, magnetic resonance imaging (MRI) examinations are based on the interactions among a primary magnetic field, a radiofrequency (RF) magnetic field, and time varying magnetic gradient fields with a gyromagnetic material having nuclear spins within a subject of interest, such as a patient. Certain gyromagnetic materials, such as hydrogen nuclei in water molecules, have characteristic behaviors in response to external magnetic fields. The precession of spins of these nuclei can be influenced by manipulation of the fields to produce RF signals that can be detected, processed, and used to reconstruct a useful image.

The magnetic fields used to generate images in MRI systems include a highly uniform, static magnetic field that is produced by a primary magnet. A series of gradient fields are produced by a set of gradient coils located around the imaging volume in which the subject is placed. The gradient fields encode positions of individual plane or volume elements (pixels or voxels) in two or three dimensions. An RF coil is employed to produce an RF magnetic field. This RF magnetic field perturbs the spins of some of the gyromagnetic nuclei from their equilibrium directions, causing the spins to precess around the axis of their equilibrium magnetization. During this precession, RF fields are emitted by the spinning, precessing nuclei and are detected by either the same transmitting RF coil, or by one or more separate coils. These signals are amplified, filtered, and digitized. The digitized signals are then processed using one or more algorithms to reconstruct a useful image.

While MRI images provide a variety of benefits and may be particularly useful for certain imaging contexts, such images may be less useful in other contexts. By way of example, while MRI images provide good spatial resolution and anatomical soft tissue contrast, such images may still be limited in their usefulness for detecting and delineating cancer lesions at an early stage, i.e., when the lesions are most easily cured and treated. That is, MRI images generated using current approaches may offer insufficient delineation of tumor and tissue boundaries for diagnostic and therapy purposes and may be unsuitable for characterization of salient characteristics for cancer diagnosis (e.g., characterization of a lesion as malignant or benign).

Conventional approaches at solving this problem have involved the introduction of contrast media to the patient. Such contrast media are based on large molecular chelates of paramagnetic ions such as Gadolinium (Gd), Manganese (Mn), or on hyperpolarized Carbon-13. Such contrast enhancement approaches, however, are invasive, involving the intravenous injection of an exogenous contrast media to the patient. As discussed herein, an MRI contrast enhancement approach that does not involve the administration of exogenous compounds is desirable.

BRIEF DESCRIPTION

In one embodiment, a magnetic resonance imaging method is provided. In accordance with this method, a tissue region undergoing imaging is treated over a range of treatment levels. Magnetic resonance images are acquired of the tissue region over the range of treatment levels. At least the magnetic resonance images are processed to track differential response observed within the magnetic resonance images over the treatment range. Based on the differential response different tissue types or cancer are characterized or differentiated with respect to generated local region.

In a further embodiment, a magnetic resonance imaging (MRI) system is provided. The MRI system includes: a primary field magnet, a plurality of gradient field coils, a radiofrequency (RF) transmit coil, an array of receiving coils, and a thermal applicator. The MRI system further includes control circuitry coupled to the gradient field coils, to the RF transmit coil, to the array of receiving coils, and to the thermal applicator. The control circuitry is configured to: adjust the temperature of a localized target tissue region over a temperature range using the thermal applicator; and acquire magnetic resonance images concurrent with the adjustment of the temperature of the localized target tissue region over the temperature range.

In an additional embodiment, a tissue evaluation method is provided. In accordance with this method, a set of magnetic resonance images acquired of a tissue region over a range of temperatures is accessed. Thermal response over the tissue region within the set of magnetic resonance images is tracked. One or more thermal response maps of the tissue region is generated based on the tracked thermal responses.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
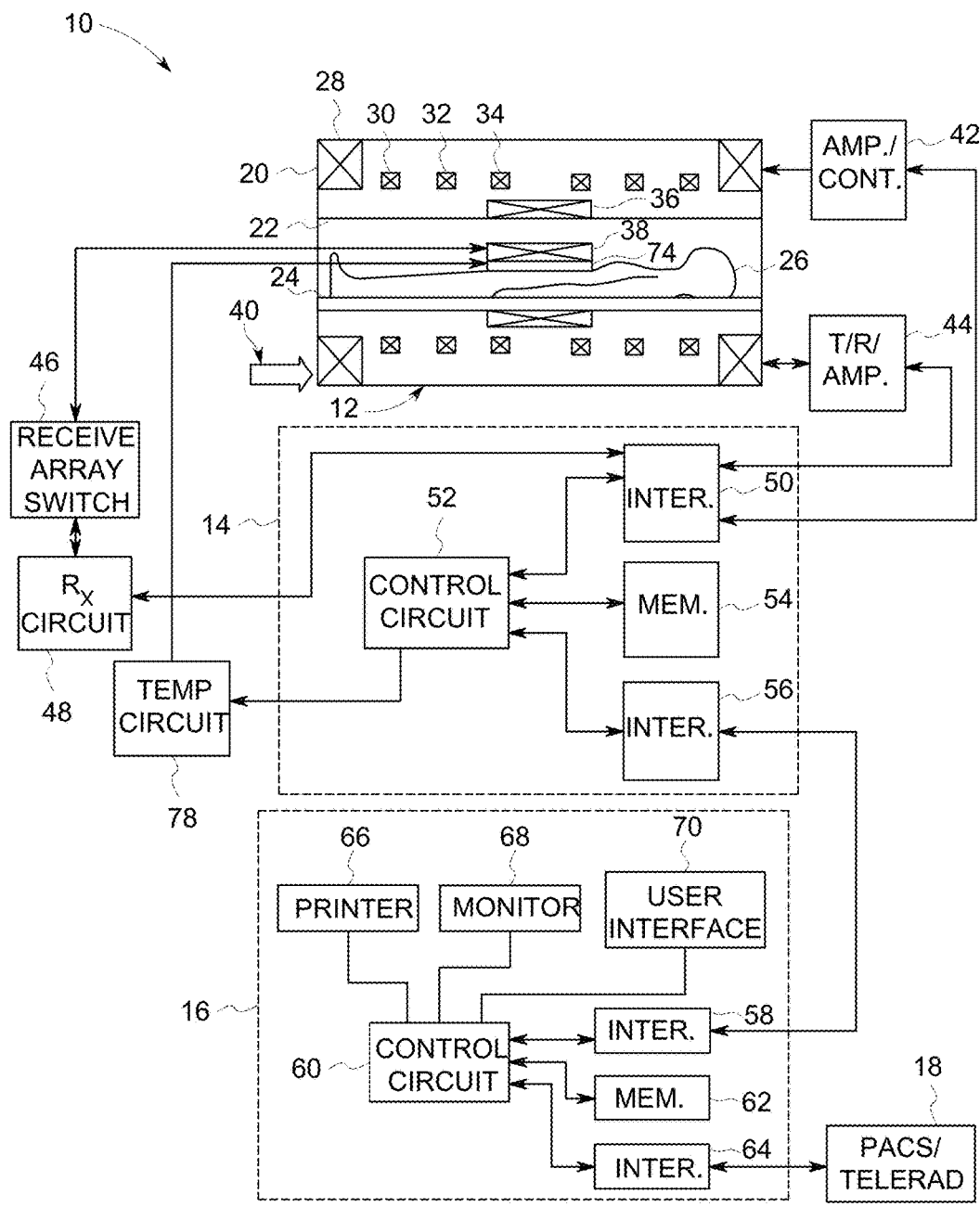
FIG. 1 is a diagrammatical illustration of an embodiment of a magnetic resonance (MR) imaging system configured to acquire MR images over a range of tissue temperatures, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Magnetic Resonance (MR) imaging provides good spatial resolution and anatomical soft tissue contrast, yet there are still limitations in detecting and delineating early-stage cancer lesions when they are curable. With this in mind, clinical applications of MR imaging in oncology (as well as in other contexts) is in the process of evolving from being a subjective and interpretive diagnostic test based on tissue morphology to a more quantitative technique probing tissue biology. In particular, there is interest in characterizing cancer in MR imaging using a multi-parametric approach, such as by supplementing conventional MRI with one or more functional MRI techniques that provide additional information related to tumor metabolism, cellular microenvironment, and/or tumor vascularity.

Traditional MR contrast enhancement techniques may facilitate acquisition of useful imaging information. Such contrast media are based on large molecular chelates of paramagnetic ions such as Gadolinium (Gd), Manganese (Mn), or hyperpolarized Carbon-13. While effective, the use of such exogenous contrast media may be undesirable due their administration via intravenous injections, which is inherently invasive.

As discussed herein, the present approach instead utilizes MR image contrast enhancement that does not require the administration of any exogenous contrast agent (e.g., Gd/Mn/$^{13}$C based drugs). By way of example, non-invasive approaches which modify the magnetic resonance signal response (such as by modifying pH, metabolic activity, metabolite concentration, mechanical structure, and so forth in the imaged region) in a determinable manner (such as heating or cooling the tissue, applying electrical voltage, applying mechanical compression or vibration) may be employed to provide MR image contrast enhancement without administration of an exogenous agent. In particular, tumors have different mechanical, water diffusion, thermal and perfusion properties from normal tissue. As discussed herein, these properties can responds differently to temperature, mechanical, or electrical changes to allow differential imaging in response to changes in these factors. By way of example, the tissue and tumor properties can produce different thermal responses in proton resonance frequency shift (PRFS)-based MR thermometry, $T_1$, $T_2$, and diffusion-weighted imaging. For example, upon heating or cooling of tissues undergoing imaging, the thermal responses of conventional MR imaging contrast mechanisms in different tissue types can contain additional information for improved delineation of tumor/tissue boundaries for diagnostic and therapy purposes, and/or for characterization of salient characteristics for cancer diagnosis, e.g., malignant versus benign tumors, use as based on characteristics such as degree of vascularization, permeability, and/or oxidative stress. Therefore, with this in mind, certain implementations of the present approach may utilize one or more of: (i) a thermal applicator, (ii) an optimized set of MR protocols that acquire $T_1$, $T_2$, and/or diffusion-weighted maps at various temperatures, and (iii) a decision-making module that interprets the acquired data. With the preceding comments in mind, though the presently described example and guidance is presented in the context of a temperature-based contrast enhancement, such discussion is provided only to facilitate and simplify explanation. It should be appreciated that the present approach is not limited by this example to temperature-based contrast enhancement, but also encompasses other techniques that might differentially modify tissue and tumor properties in a manner discernible by MR, including, but not limited to, application of different levels of electrical (e.g., voltage) or mechanical (e.g., compression or vibration) treatment during image acquisition.

By way of introduction to the above-referenced concepts, the presently described approaches may be performed using a magnetic resonance imaging (MRI) system on which specific imaging routines are initiated by a user (e.g., a radiologist). The MRI system may perform data acquisition, data construction, image reconstruction/synthesis, and image processing. Accordingly, referring to FIG. 1, an example of a suitable magnetic resonance imaging system 10 is illustrated schematically as including a scanner 12, a scanner control circuit 14, and system control circuitry 16. System 10 additionally includes remote access and storage systems or devices as picture archiving and communication systems (PACS) 18, or other devices such as teleradiology equipment so that data acquired by the system 10 may be accessed on- or off-site. While the MRI system 10 may include any suitable scanner or detector, in the illustrated embodiment, the system 10 includes a full body scanner 12 having a housing 20 through which a bore 22 is formed. A table 24 is moveable into the bore 22 to permit a patient 26 to be positioned therein for imaging selected anatomy within the patient 26. The selected anatomy may be imaged by a combination of patient positioning, selected excitation of certain gyromagnetic nuclei within the patient 26, and by using certain features for receiving data from the excited nuclei as they spin and precess, as described below.

Scanner 12 includes a series of associated coils for producing controlled magnetic fields for exciting the gyromagnetic material within the anatomy of the subject being imaged. Specifically, a primary magnet coil 28 is provided for generating a primary magnetic field generally aligned with the bore 22. A series of gradient coils 30, 32, and 34 permit controlled magnetic gradient fields to be generated for positional encoding of certain of the gyromagnetic nuclei within the patient 26 during examination sequences. A radio frequency (RF) coil 36 is provided, and is configured to generate radio frequency pulses for exciting the certain gyromagnetic nuclei within the patient.

In addition to the coils that may be local to the scanner 12, the system 10 also includes a separate set of receiving coils 38 (e.g., a phased array of coils) configured for placement proximal (e.g., against) the patient 26. The receiving coils 38 may have any geometry, including both enclosed and single-sided geometries. As an example, the receiving coils 38 can include cervical/thoracic/lumbar (CTL) coils, head coils, single-sided spine coils, and so forth. Generally, the receiving coils 38 are placed close to or on top of the patient 26 so as to receive the weak RF signals (weak relative to the transmitted pulses generated by the scanner coils) that are generated by certain of the gyromagnetic nuclei within the patient 26 as they return to their relaxed state. The receiving coils 38 may be switched off so as not to receive or resonate with the transmit pulses generated by the scanner coils, and may be switched on so as to receive or resonate with the RF signals generated by the relaxing gyromagnetic nuclei.

In addition, proximate to the receiving coil 38, the depicted embodiment includes a thermal applicator 74 (here depicted as a pad contacting the patient). The thermal applicator 74, as discussed herein may be used to heat and/or cool the imaged tissues over a given range (e.g., a 5° C., 6°

C., 8° C., or 10° C. range, and so forth) over the course of an image acquisition procedure. In this manner, MR image data may be acquired of the tissues at different temperatures along the range allowed by the applicator 74. As will be appreciated, though the applicator 74 is depicted in the form of a pad, other structures or interfaces (such as an insertable probe or bottle which may be heated or cooled) may be suitable for temperature control at the desired tissue. For example, pads and so forth may be suitable for surface temperature adjustments, while insertable probes and so forth may be used for internal temperature heating and cooling of imaged tissues. Examples of techniques by which the applicator 74 may vary temperature include, but are not limited to: hot or cool water flow through tubes lines, resistive coil elements (which are MR compatible) which apply heat when current is applied, hot or cool air blown onto the region of interest, application of focused ultrasound or radiofrequency (RF) radiation at the tissue site of interest. Each of these approaches may be regulated in response to the measurements or feedback provided by one or more temperature probe sensors situated at the region of interest.

Control and operation of the applicator 74 may be performed by a temperature circuit 78. In the depicted embodiment, the temperature circuit is in communication with and controlled by the control circuit 52 of the imaging system. In other embodiments, however, the temperature circuit 78 may be operated independent of the MR imaging system 10 while still providing the benefits discussed herein.

The various coils of system 10 are controlled by external circuitry to generate the desired field and pulses, and to read emissions from the gyromagnetic material in a controlled manner. In the illustrated embodiment, a main power supply 40 provides power to the primary field coil 28. A driver circuit 42 is provided for pulsing the gradient field coils 30, 32, and 34, such as using the waveforms and pulse sequences as discussed herein. Such a circuit may include amplification and control circuitry for supplying current to the coils as defined by digitized pulse sequences output by the scanner control circuit 14. Another control circuit 44 is provided for regulating operation of the RF coil 36. Circuit 44 includes a switching device for alternating between the active and inactive modes of operation, wherein the RF coil 36 transmits and does not transmit signals, respectively. Circuit 44 also includes amplification circuitry for generating the RF pulses. Similarly, the receiving coils 38 are connected to switch 46 that is capable of switching the receiving coils 38 between receiving and non-receiving modes such that the receiving coils 38 resonate with the RF signals produced by relaxing gyromagnetic nuclei from within the patient 26 while in the receiving state, and they do not resonate with RF energy from the transmitting coils (i.e., coil 36) so as to prevent undesirable operation while in the non-receiving state. Additionally, a receiving circuit 48 is provided for receiving the data detected by the receiving coils 38, and may include one or more multiplexing and/or amplification circuits.

Scanner control circuit 14 includes an interface circuit 50 for outputting signals for driving the gradient field coils 30, 32, 34 and the RF coil 36. Additionally, interface circuit 50 receives the data representative of the magnetic resonance signals produced in examination sequences from the receiving circuitry 48 and/or the receiving coils 38. The interface circuit 50 is operatively connected to a control circuit 52. The control circuit 52 executes the commands for driving the circuit 42 and circuit 44 based on defined protocols selected via system control circuit 16. Control circuit 52 also serves to provide timing signals to the switch 46 so as to synchronize the transmission and reception of RF energy. Further, control circuit 52 receives the magnetic resonance signals and may perform subsequent processing before transmitting the data to system control circuit 16. Scanner control circuit 14 also includes one or more memory circuits 54, which store configuration parameters, pulse sequence descriptions, examination results, and so forth, during operation. The memory circuits 54, in certain embodiments, may store instructions for implementing at least a portion of the image processing techniques described herein.

Interface circuit 56 is coupled to the control circuit 52 for exchanging data between scanner control circuit 14 and system control circuit 16. Such data may include selection of specific examination sequences to be performed, configuration parameters of these sequences, and acquired data, which may be transmitted in raw or processed form from scanner control circuit 14 for subsequent processing, storage, transmission and display.

An interface circuit 58 of the system control circuit 16 receives data from the scanner control circuit 14 and transmits data and commands back to the scanner control circuit 14. The interface circuit 58 is coupled to a control circuit 60, which may include one or more processing circuits in a multi-purpose or application specific computer or workstation. Control circuit 60 is coupled to a memory circuit 62, which stores programming code for operation of the MRI system 10 and, in some configurations, the image data for later reconstruction, display and transmission. An additional interface circuit 64 may be provided for exchanging image data, configuration parameters, and so forth with external system components such as remote access and storage devices 18. Finally, the system control circuit 60 may include various peripheral devices for facilitating operator interface and for producing hard copies of the reconstructed images. In the illustrated embodiment, these peripherals include a printer 66, a monitor 68, and user interface 70 including devices such as a keyboard or a mouse.

It should be noted that subsequent to the acquisitions described herein, the system 10 may simply store the acquired data for later access locally and/or remotely, for example in a memory circuit (e.g., memory 56, 62). Thus, when accessed locally and/or remotely, the acquired data may be manipulated by one or more processors contained within an application-specific or general-purpose computer. The one or more processors may access the acquired data and execute routines stored on one or more non-transitory, machine readable media collectively storing instructions for performing methods including the image acquisition, processing, and/or reconstruction steps described herein.

Figure 2:
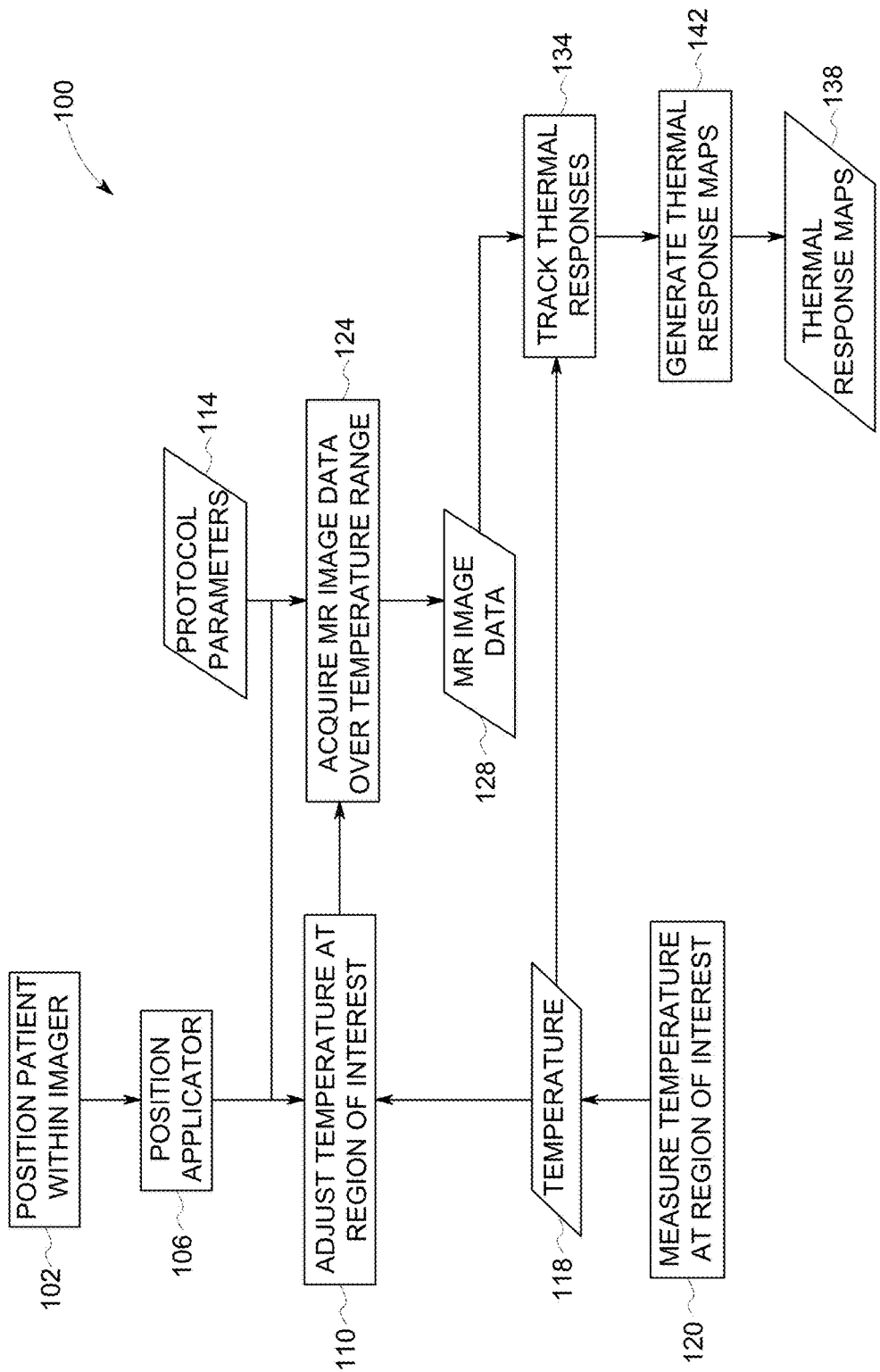
FIG. 2 depicts a process flow diagram for acquiring and analyzing MR images over a range of tissue temperatures, in accordance with an aspect of the present disclosure.

With the preceding in mind, and turning to FIG. 2, an example of a process flow 100 in accordance with the present approach is depicted. In this example, a patient 26 is positioned (block 102) within an MR imager. A thermal applicator 74 is positioned (block 106) on, around, or in the patient so as to be able to modulate the temperature of the tissue at the imaging site within a specified temperature range. For example, positioning the thermal applicator may, depending on the embodiment, involve, placing a heating or cooling pad on the patient 26, positioning a heating or cooling probe within the patient proximate to the region of interest, and/or positioning an RF or ultrasound emitter so as to focus energy at the region of interest.

In the depicted example, subsequent to the positioning of the applicator 74, the temperature at the region of interest is modulated (block 110). In certain implementations, the adjustment of temperature at the region of interest is performed in accord with one or more protocol parameters 114 associated with the prescribed acquisition. Such protocol parameters 114 may specify one or more of the range of temperature change which tissue undergoing imaging is to undergo, the absolute temperature values to be observed along with timing and duration, the rate of temperature change, and so forth. As part of the temperature adjustment process, the temperature 118 at the region of interest may be measured (block 120), such as using one or more temperature sensors positioned at or near the region of interest. In certain embodiments, as part of the initial or ongoing temperature adjustment process, the region being imaged may be stabilized at a given temperature (such as an initial temperature) for approximately 5-10 minutes to achieve steady state prior to imaging.

In the depicted example, the protocol parameters 114 also specify parameters for the acquisition (block 124) of MR image data 128. For example, the parameters 114 may specify, timing, contrast, pulse sequences, and so forth to be employed to acquire the MR image data 128. As a result of the preceding steps, MR image data 128 may be acquired using a desired contrast scheme over a specified tissue temperature range.

The acquired image data may be processed, such as by a dedicated or programmed processing module, to track (block 134) thermal responses within the acquired images. In certain embodiments, the measured temperatures 118 may be input to the tracking process such that measured temperature and observed MR response are available for a series of time points. In other embodiments, the MR image data alone may be employed along with the expected relative temperature differences associated with the images for a given protocol. By way of example, a thermally sensitive nuclear magnetic resonance (NMR) parameter ($\Gamma$) of interest for the respective contrast acquisition (e.g., $T_1$, $T_2$, $T_2^*$, proton resonance frequency shift (PRFS), apparent diffusion coefficient (ADC), and so forth) may be tracked and/or evaluated at different temperatures (T) at which the tissue was imaged (i.e., $\Delta\Gamma(T)$).

Based on the tracked thermal responses, one or more thermal response maps 138 may be generated (block 142) and used in delineating and/or characterizing tissue regions (e.g., tumors or lesions) of interest. In certain embodiments, such maps may depict $\Delta\Gamma(T)/T$ (e.g., the change in $\Gamma$ (such as $T_1$) as a function of temperature (T)) for each pixel in the image (i.e., on a pixel-by-pixel basis). The maps may then, as discussed herein, be used in characterizing imaged tumors as benign or malignant as well as determining the boundaries of such tumors. For example, the maps of $\Delta\Gamma(T)/T$ (e.g., $\Delta T_1/T$) may be used to identify tumors, including characterizing malignant tumors, based on an elevated $\Delta T_1/T$ value. In this manner, the generated maps (or other outputs) may be used to automatically characterize a tissue of interest, (e.g., a malignant tumor) using a simple thresholding technique or by setting a threshold of some set amount (e.g., one standard deviation, two standard deviations, and so forth) above an observed mean. In one embodiment, the tumor tissue can be differentiated and characterized by first changing the regional tissue temperature (such as using applicator 74) to above or below the normal range and then observing the rate of change in temperature as the tissue returns to normal.

With the preceding general discussion in mind, studies were performed to evaluate the efficacy of the present thermal contrast approach. In one such study, rat malignant breast adenocarcinoma (tumor 1), rat benign breast fiberadenoma (tumor 2), and rat prostate carcinoma (tumor 3) cells were cultured and used to inoculate female Fischer 344 rats (tumor 1, 2) and male Copenhagen rats (tumor 3). Tumors were grown on the rat flanks and imaged when they reached a size of 2-3 cm. Imaging tests were performed on the in vivo tissue samples of tumor 1, muscle tissue directly surrounding tumor 1 (muscle 1), tumor 2, muscle tissue directly surrounding tumor 2 (muscle 2), tumor 3, and its corresponding muscle tissue (muscle 3). The core body temperature of the rats were raised and maintained at various temperatures from ~25° C. to ~40° C. Two cycles of cooling and warming were performed per rat. To ensure reproducibility, data was acquired for multiple rats containing tumor types 1-3.

Images were acquired on a 3T GE MR750 scanner (GE Healthcare, Waukesha, Wis.). $T_1$ data sets were acquired using a 2D axial inversion recovery (IR) sequence at the following TI values: 3500, 950, 550, 350, 150 with all times in ms. Other parameters included flip angle ($\theta$)=180°/90° set with proper TG, TR=4000 ms, TE=min, freq FoV=13 cm, phase FoV=6.5 cm, matrix 128×128, NEX=1, 5 slices, 4 mm thick. $T_1$-IR signal intensity (S) was fit either for a selected region of interest (ROI) or per pixel to $S(\tau)=S_0(1-2 \cdot e^{-\tau/T_1})$ where ($\tau$) is the inversion time. $T_2$ data sets were acquired using a 2D axial spin echo (SE) sequence with the following TE values: 300, 150, 100, 50, and 4 ms ($\theta$=90°/180° set with proper TG, and same parameters as IR). $T_2$-SE signal intensity (S) was fit either for a selected ROI or per pixel to $S(\tau)=S_0 \cdot e^{-\tau_E/T_2}$ where ($\tau_E$) is the echo time.

Figure 3:
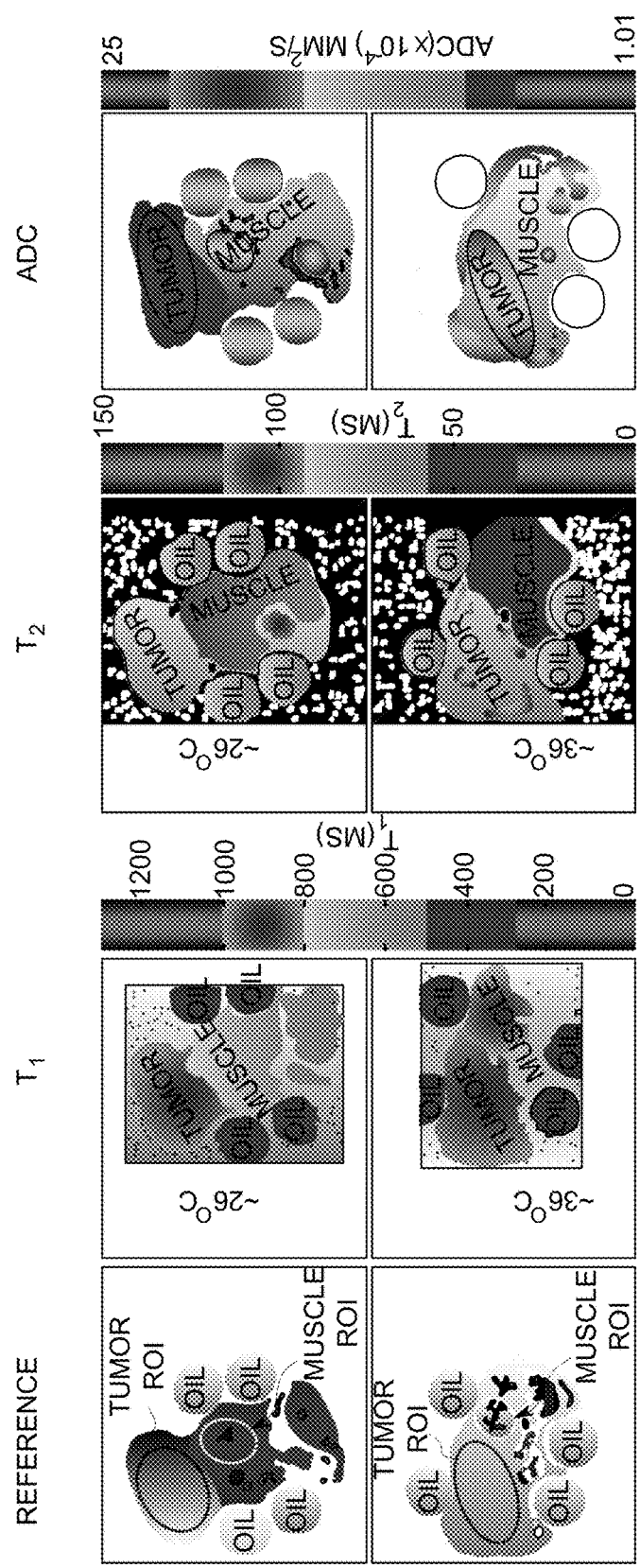
FIG. 3 depicts grayscale representations of reference images and MR images acquired of a tumor over a range of temperatures, in accordance with an aspect of the present disclosure.

Representative images from this study are shown in FIG. 3. In these depictions, the leftmost images (top and bottom) are reference axial images through the center slice of tumor 1. The remaining images in the top row (i.e., top row images in the $T_1$, $T_2$, and ADC columns) are quantitative $T_1$, $T_2$, and ADC maps at ~26° C. The remaining images in the bottom row (i.e., bottom row images in the $T_1$, $T_2$, and ADC columns) are quantitative $T_1$, $T_2$, and ADC maps at ~36° C. General locations of the tumor and muscle regions are indicated on the images by annotation. Oil vials were inserted and used as a calibrated validation of measurement accuracy. As can be seen in the images, tumor and other tissues may be delineated and characterized in the respective images acquired at different tissue temperatures.

Figure 4:
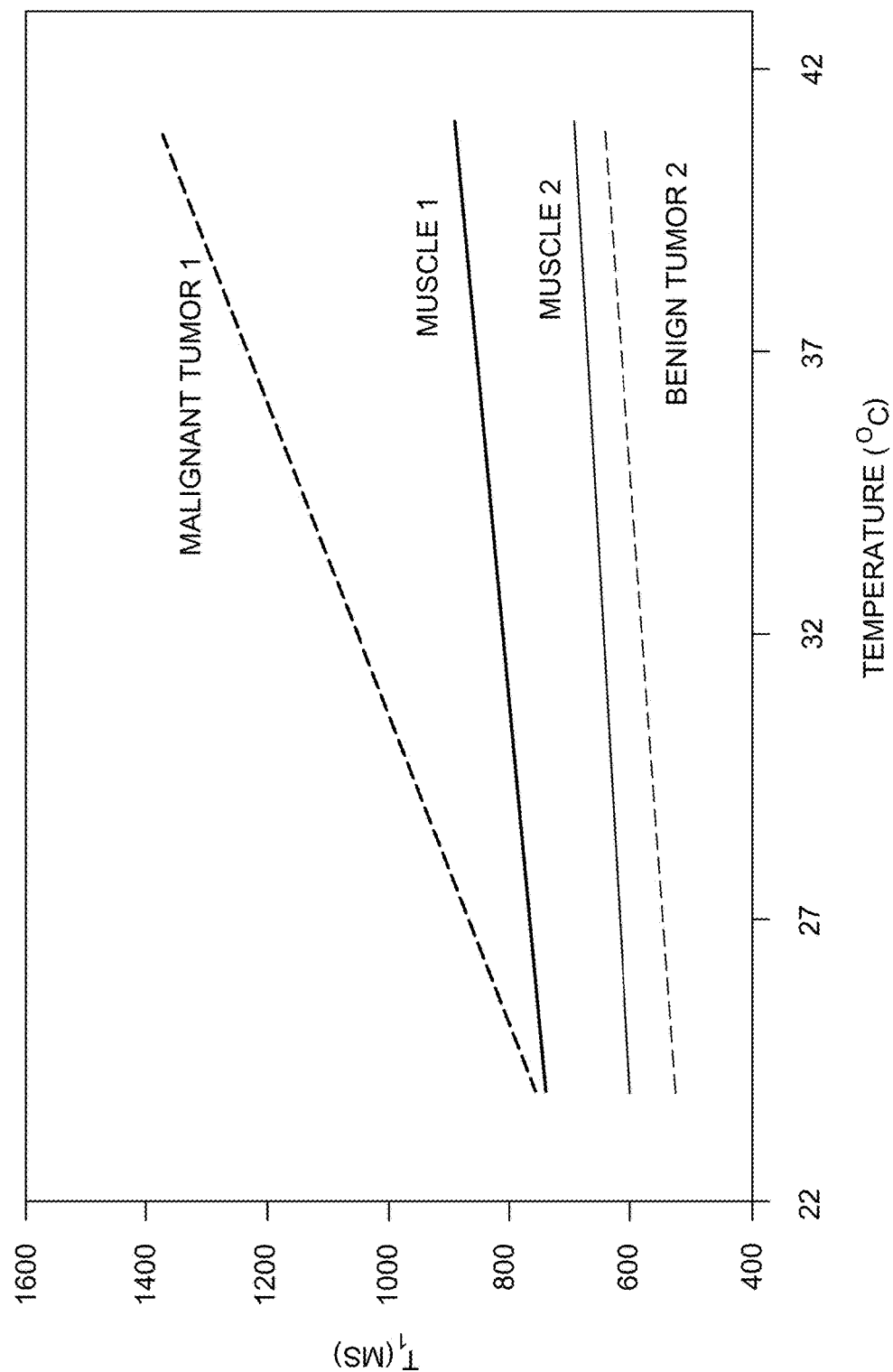
FIG. 4 depicts a graph that plots $\Delta T_1$ as a function of temperature for tumor/muscle 1 and tumor/muscle 2, in accordance with an aspect of the present disclosure.

Turning to FIG. 4, this figure depicts a graph that plots $\Delta T_1$ as a function of temperature for tumor/muscle 1 and tumor/muscle 2. In particular, the average $T_1$ measured over the corresponding 5 slices for the tumor and muscle ROIs of tumor 1 and 2 is plotted. In the depicted graph, the slopes of the curves indicate that a different $T_1$ contrast can be achieved by varying the temperature of the tissue. In these results, the $\Delta T_1/°$ C. for malignant breast tumor is more than 4 times greater than that of benign breast tumor and muscle tissue. Thus, per thee results, thermal contrast can be used (1) to delineate between tumor and muscle regions for assessing tumor boundaries, and (2) for characterization of malignant versus benign tumors in the case of tumor 1 and tumor 2.

Similar plots to FIG. 4 were made for $T_2$ and ADC for all tumor/muscle types. A full data summary is presented in Table 1 (below), showing the potential heat-induced contrast through a $T_1$, $T_2$, or ADC based mechanism. In particular, Table 1 summarizes the experimental data acquired for quantitative relaxation parameter and ADC change as a function of temperature for tumors 1-3.

TABLE 1

| | Tumor (Δ %/° C.) | | | Muscle (Δ %/° C.) | | |
|---|---|---|---|---|---|---|
| | $T_1$ | $T_2$ | ADC | $T_1$ | $T_2$ | ADC |
| Breast Malignant | 4.5 | 3.2 | 4.2 | 1.2 | <1 | 1.3 |
| Breast Benign | 1.2 | <1 | 6 | 1 | <1 | 1.7 |
| Prostate Malignant | 1.6 | 5 | 2.6 | 1.2 | <1 | 1.5 |

As will be appreciated, overall the data supports the use of heat-induced thermal contrast as an imaging mechanism to aid in the delineation and characterization of tumors. In particular, the summarized data shows that thermal responses of some of the contrast types (i.e., $T_1$, $T_2$, or ADC) provide additional information that can potentially improve visualization or characterization of tumors. For example, Table indicates that a malignant breast tumor exhibited more than 4 times change in $T_1$ per degree Celsius rise in tissue temperature compared to that in a benign breast tumor. The change in $T_2$ per degree Celsius in malignant prostate tumor is also observed to be approximately five times that of muscle tissue. These results indicate the possibility of delineating and/or characterizing tumor tissue using differential thermal response of these tissues that is observable using different MR contrast imaging approaches.

Technical effects of the invention include non-invasive approaches for delineating and characterizing tissue using MR imaging over a range of tissue temperatures or other treatments (e.g., electrical or mechanical treatments). By way of example, tumor tissue may be distinguished and delineated from other tissue, such as muscle tissue. Further, tumor tissue may be characterized as malignant or benign using such approaches.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A magnetic resonance imaging method, comprising:
heating or cooling a tissue region undergoing imaging over a range of temperatures;
acquiring magnetic resonance images of the tissue region over the range of temperatures;
processing at least the magnetic resonance images to track differential response observed within the magnetic resonance images over the range of temperatures, which comprises determining, on a pixel-by-pixel basis, the change in a thermally sensitive nuclear magnetic resonance parameter of interest over the rage of temperatures; and
based on the differential response characterizing or differentiating different tissue types or cancer with respect to a local region.

2. The method of claim 1, further comprising treating the tissue region by applying one or more of an electrical voltage, a mechanical compression, or a mechanical vibration to the tissue region over a range of treatment levels.

3. The method of claim 1, wherein heating or cooling the tissue region comprises applying a pad or probe adjacent or proximate to the tissue region, wherein the pad or probe employ one or more of a flow of heated or cooled water or resistive heating elements to change the temperature of the tissue region.

4. The method of claim 1, wherein heating or cooling the tissue region comprises applying ultrasound or radiofrequency radiation or any other suitable technique for directed tissue heating or cooling to the tissue region.

5. The method of claim 1, wherein heating or cooling the tissue region over the range of temperatures comprises cooling the temperature region to a lower end of the range and allowing the temperature of the tissue region to raise to a normal temperature or heating the temperature region to an upper end of the range and allowing the temperature of the tissue region to lower to the normal temperature.

6. The method of claim 1, further comprising:
acquiring temperature readings concurrent with magnetic resonance images; and
processing both the magnetic resonance images and the temperature readings to characterize or differentiate the different tissue types of cancer.

7. The method of claim 6, further comprising controlling heating or cooling of the tissue region over the range of temperatures using the temperature readings.

8. The method of claim 1, wherein acquiring magnetic resonance images comprises acquiring magnetic resonance images using a respective contrast acquisition comprising one or more of a $T_1$, a $T_2$, a $T_2^*$, a proton resonance frequency shift (PRFS), or an apparent diffusion coefficient (ADC) acquisition.

9. The method of claim 1, wherein processing the magnetic resonance images to track differential response comprises generating thermal response maps corresponding to the pixels of the magnetic resonance images.

10. The method of claim 1, wherein characterizing or differentiating different tissue types or cancer comprises one or both of delineating a tumor region or characterizing a tumor region as benign or malignant based on one or more of degree of vascularization, permeability, or oxidative stress.

* * * * *